US008396671B2

(12) United States Patent
Jojic et al.

(10) Patent No.: US 8,396,671 B2
(45) Date of Patent: Mar. 12, 2013

(54) CLUSTER MODELING, AND LEARNING CLUSTER SPECIFIC PARAMETERS OF AN ADAPTIVE DOUBLE THREADING MODEL

(75) Inventors: Nebojsa Jojic, Redmond, WA (US); David E. Heckerman, Bellevue, WA (US); Manuel Jesus Reyes Gomez, Kirkland, WA (US)

(73) Assignee: Microsoft Corporation, Redmond, WA (US)

( * ) Notice: Subject to any disclaimer, the term of this patent is extended or adjusted under 35 U.S.C. 154(b) by 1272 days.

(21) Appl. No.: 11/770,684

(22) Filed: Jun. 28, 2007

(65) Prior Publication Data

US 2008/0021686 A1    Jan. 24, 2008

Related U.S. Application Data

(63) Continuation-in-part of application No. 11/356,196, filed on Feb. 16, 2006, now abandoned.

(51) Int. Cl.
    *G01N 33/48* (2006.01)
(52) U.S. Cl. ........................................................ 702/19
(58) Field of Classification Search .................. 702/19
    See application file for complete search history.

(56) References Cited

U.S. PATENT DOCUMENTS

| 5,933,819 | A  | 8/1999  | Skolnick et al. |
| 6,861,234 | B1 | 3/2005  | Simard et al. |
| 6,895,396 | B2 | 5/2005  | Schwartz et al. |
| 7,094,555 | B2 | 8/2006  | Kwok et al. |
| 2004/0072162 | A1 | 4/2004 | Fomsagaard et al. |
| 2004/0072246 | A1 | 4/2004 | Martin et al. |
| 2004/0072249 | A1 | 4/2004 | Hoffman et al. |
| 2004/0137537 | A1 | 7/2004 | Montero-Julian et al. |
| 2005/0074809 | A1 | 4/2005 | Brusic |
| 2005/0074813 | A1 | 4/2005 | Nauss et al. |
| 2005/0079549 | A1 | 4/2005 | Castracane |
| 2005/0095655 | A1 | 5/2005 | Montero-Julian et al. |
| 2006/0057673 | A1 | 3/2006 | Liu et al. |
| 2006/0084116 | A1 | 4/2006 | Muchhal |
| 2006/0111554 | A1 | 5/2006 | Lasters et al. |
| 2006/0160071 | A1 | 7/2006 | Heckerman et al. |
| 2006/0257944 | A1 | 11/2006 | Fridman et al. |
| 2007/0005262 | A1 | 1/2007 | Gershoni et al. |
| 2007/0154953 | A1 | 7/2007 | Brunner et al. |

FOREIGN PATENT DOCUMENTS

| WO | 9859244       | 12/1998 |
| WO | 0220564 A2    | 3/2002  |
| WO | 2005038429 A2 | 4/2005  |

OTHER PUBLICATIONS

Gotoh et al. (Adv. Biophys., vol. 36, pp. 159-206,1999).*
Lund et al. (Immunogenetics, vol. 55, p. 797-810, 2004).*
Tsuda et al. (Bioinformatics vol. 18, Sup. 1, S268-s275, 2002).*
Park et al. (Proteins: Structure, Function, and Genetics vol. 40, p. 237-248, 2000).*
Florea et al. (Proceedings of the Computational Systems Bioinformatics (CSB'03), pp. 10, 2003).*
Mallios et al. (Bioinformatics, vol. 17, No. 10, p. 942-948, 2001).*
Kratochwil, Nicole A. et al. Predicting plasma protein binding of drugs: a new approach. Biochemical Pharmacology. Nov. 1, 2002, vol. 64, Issue 9, pp. 1355-1374.
Rubin, G. M. et al. An expectation maximization algorithm for training hidden substitution models. Journal of Molecular Biology. Apr. 12, 2002, vol. 317, Issue 5, pp. 753-764.
International Search Report and Written Opinion dated Oct. 9, 2008 for PCT Application Serial No. PCT/US2008/060945, 11 Pages.
Miyazawa, et al., J. Mol. Biol., vol. 256, p. 623-644, 1996.
Specific weight. (1992). In Academic Press Dictionary of Science and Technology. Retrieved Jun. 25, 2008, from http://www.credoreference.com/entry/3161132.
Density. (1992). In Academic Press Dictionary of Science and Technology. Retrieved Jun. 25, 2008, from http://www.credoreference.com/entry/3094286.
OA mailed Jul. 7, 2008 for U.S. Appl. No. 11/356,196, 22 pages.
Brusic, et al. "Prediction of MHC Binding Peptides Using Artificial Neural Networks", Complexity International, Apr. 1995, vol. 02, http://www.complexity.org.au/ci/vol02/vbb/vbb.html, last accessed Jan. 24, 2007, 10 pages.
Peters, et al. "A Community Resource Benchmarking Predictions of Peptide Binding to MHC-I Molecules", http://mhcbindingpredictions.immuneepitope.org/manuscript.pdf, accessed Jan. 24, 2007, 51 pages.
Yanover, et al. "Predicting Protein-Peptide Binding Affinity by Learning Peptide-Peptide Distance Functions", Predicting Binding Affinity by Learning Distance Functioning, pp. 456-471, last accessed Jan. 24, 2007.
Zhu, et al. "Improving Prediction of MHC Class I Binding Peptides with Additional Binding Data", https://www.jsbi.org/journal/GIW04/GIW04P127.pdf, last accessed Jan. 24, 2007, 2 pages.
Hertz, et al. PepDist: a new framework for protein-peptide binding prediction based on learning peptide distance functions. BMC Bioinformatics. Mar. 20, 2006;7 Suppl 1:S3.
Sette, et al. Nine major HLA class I supertypes account for the vast preponderance of HLA-A and -B polymorphism, Immunogenetics, Nov. 1999 50:201-212.
Jones, et al. "A new approach to protein fold recognition," Nature (1992) 358:86-89.
Melo, et al. "Statistical potentials for fold assessment," Protein Science (2002) 11:430-448.
Chang, et al. Predicting peptides bound to I-Ag7 class II histocompatibility molecules using a novel expectation-maximization alignment algorithm. Proteomics 2007, 7, 367-377.

(Continued)

*Primary Examiner* — Jerry Lin
(74) *Attorney, Agent, or Firm* — Lee & Hayes, PLLC

(57) ABSTRACT

Cluster models are described herein. By way of example, a system for predicting binding information relating to a binding of a protein and a ligand can include a trained binding model and a prediction component. The trained binding model can include a probability distribution and a hidden variable that represents a cluster of protein sequences, and/or a set of hidden variables representing learned supertypes. The prediction component can be configured to predict the binding information by employing information about the protein's sequence, the ligand's sequence and the trained binding model.

20 Claims, 6 Drawing Sheets

OTHER PUBLICATIONS

Jojic, et al. "Topographic transformation as a discrete latent varaible," Neural Information Processing Systems (NIPS) '99,Nov. 1999, Denver, CO.

Stern, et al. Peptide 15-mers of defined sequence that substitute for random amino acid copolymers in amelioration of experimental autoimmune encephalomyelitis. Proc Natl Acad Sci U S A. Feb. 1, 2005;102(5):1620-5. Epub Jan. 21, 2005.

Karpenko, et al. Prediction of MHC class II binders using the ant colony search strategy. Artif Intell Med. Sep.-Oct. 2005; 35(1-2):147-56.

Reche, et al. Enhancement to the RANKPEP resource for the prediction of peptide binding to MHC molecules using profiles. Immunogenetics. Sep. 2004;56(6):405-19. Epub Sep. 3, 2004.

Nielsen, et al. Improved prediction of MHC class I and class II epitopes using a novel Gibbs sampling approach. Bioinformatics. Jun. 12, 2004;20(9):1388-97. Epub Feb. 12, 2004.

Davies, et al. A novel predictive technique for the MHC class II peptide-binding interaction. Mol Med. Sep.-Dec. 2003;9 (9-12):220-5.

Murugan, et al. Prediction of MHC class II binding peptides based on an iterative learning model. Immunome Res. Dec. 13, 2005;1:6.

Brusic, et al. Prediction of MHC class II-binding peptides using an evolutionary algorithm and artificial neural network. Bioinformatics. 1998;14(2):121-30.

N. Jojic, et al., "Using "epitomes" to model genetic diversity: Rational design of HIV vaccine cocktails,", in Advances in Neural Information Processing Systems 18, Presented at NIPS 2005, 8 pages.

O. Schueler-Furman, et al., "Structure-based prediction of binding peptides to MHC class I molecules: Application to a broad range of MHC alleles," Protein Science, 2000, pp. 1838-1846, vol. 9.

A. Sette, et al., "Peptide binding to the most frequent HLA-A class I alleles measured by quantitative molecular binding assays," Molecular Immunology, 1994, pp. 813-822, vol. 31, No. 11.

M. Bhasin, et al., "MHCBN: A comprehensive database of MHC binding and non binding peptides," Bioinformatics, 2003, pp. 665-666, vol. 19, No. 5.

H. Rammensee, et al., "SYFPEITHI: database for MHC ligands and peptide motifs," Immmunogenetics, 1999, pp. 213-219, vol. 50.

C. Moore, et al., "Evidence of HIV-1 Adaptation to HLA-Restricted Immune Responses at a Population Level," Science, May 24, 2002, pp. 1439-1443, vol. 296.

C. Yanover, et al., "Predicting protein-peptide binding affinity by learning peptide-peptide distance functions," Recomb, 2005, pp. 456-471.

K. Arien, et al., "Replicative fitness of historical and recent HIV-1 isolates suggest HIV-1 attenuation over time," AIDS, Oct. 14, 2005, pp. 1555-1564, vol. 19.

N. Jojic, et al., "Learning MHC I-peptide binding", Bioinformatics, vol. 22 No. 14 2006, pp. e227-e235.

H. Singh, et al., "ProPred: prediction of HLA-DR binding sites", Bioinformatics Applications Note, vol. 17, No. 12, 2001, pp. 1236-1237.

Altuvia et al. (1997). Human Immunology, vol. 58, pp. 1-11.

Wojciechowski et al. (2001). J. Comput. Chem., vol. 23, pp. 189-197.

Lee, et al. Biophysical Chemistry, vol. 115, p. 209-214. Jan. 6, 2005.

Deng, et al. J. Chem. Inf. Comput. Sci. vol. 44, pp. 699-703, 2004.

Park, et al. Proteins, vol. 40, pp. 237-248. 2000.

Marshall, et al. Proteomics and Protein-Protein Interactions: Biology chemistry, bioinformatics and Drug Design, Chapter 2, pp. 115-146. 2005.

Altuvia, et al. Methods, vol. 34, pp. 454-459. 2004.

Wiesmuller, et al. Biol. Chem. vol. 382, pp. 571-579. 2001.

Lazaridis et al., "Effective Energy Functions for Protein Structure Prediction", Theory and Simulation, http://www.sci.ccny.cuny.edu/~themis/curropin.pdf, last accessed Jan. 24, 2007, 7 pages.

Lilien, et al. "A Novel Ensemble Based Scoring and Search Algorithm for Protein Redesign, and Its Application to Modify the Substrate Specificity of the Gramicidin Synthetase A Phenylalanine Adenylation Enzyme", http://delivery.acm.org/10.1145/980000/974622/p46-lilien.pdf?key1=974622&key2=3858269611&coll=GUIDE&dl=GUIDE&CFID=75919783&CFTOKEN=92791909, last accessed Jan. 24, 2007, 12 pages.

Zhao, et al. "Application of Support Vector Machines for T-cell Epitopes Prediction", Bioinformatics, Apr. 7, 2003, vol. 19 No. 15 2003, pp. 1978-1984, http://bioinformatics.oxfordjournals.org/cgi/reprint/19/15/1978, last accessed Jan. 24, 2007, 7 pages.

Brusic, et al., "Prediction of Promiscuous Peptides that Bind HLA Class I Molecules", Immunology and Cell Biology, 2002, vol. 80, Issue 3, pp. 280-285.

Heckerman, et al., "Leveraging Information Across HLA Alleles/Supertypes Improves Epitope Prediction", Springer Berlin/Heidelberg, Research in Computational Molecular Biology, Lecture Notes in Computer Science, 2006, vol. 3909, pp. 296-308.

Jacob, et al., "Epitope Prediction Improved by Multitask Support Vector Machines", Retrieved on Feb. 6, 2007, Available at <<http://hal.archives-ouvertes.fr/docs/00/12/90/62/PDF/mtkepitope-jacob-vert.pdf>>, 18 pgs.

Jain, "Scoring Noncovalent Protein-Ligand Interactions: A Continuous Differentiable Function Tuned to Compute Binding Affinities", Springer Netherlands, Journal of Computer-Aided Molecular Design, 1996, vol. 10, No. 5, pp. 427-440.

Jurs, et al., "Studies of Chemical Structure-Biological Activity Relations Using Pattern Recognition", ACS Symposium Series, 1979, vol. 112, Computer-Assisted Drug Design, Chapter 4, pp. 103-129.

Lee, et al., "Learning With Positive and Unlabeled Examples Using Weighted Logistic Regression", In the Proceedings of the Twentieth International Conference on Machine Learning, 2003, 8 pgs.

Qu, et al., "Bayesian Protein Family Classifier", AAAI Press, In the Proceedings of the 6th International Conference on Intelligent Systems for Molecular Biology, 1998, pp. 131-139 (9 pgs.).

Rousseeuw, et al., "Robustness Against Separation and Outliers in Logistic Regression", Elsevier Science Publishers B.V., Computational Statistics & Data Analysis, 2003, vol. 43, Issue 3, pp. 315-332.

Tandon, et. al., "Predicting Continuous Epitopes in Proteins", IEEE, In the Proceedings of the Computational Systems Bioinformatics Conference, 2005, pp. 133-134 (2 pgs.).

Williams, et al., "Incomplete-Data Classification Using Logistic Regression", ACM, In the Proceedings of the 22nd International Conference on Machine Learning, 2005, pp. 972-979.

Xiao, et al., "Prediction of Genomewide Conserved Epitope Profiles of HIV-1: Classifier Choice and Peptide Representation", Statistical Applications in Genetics and Molecular Biology, 2005, vol. 4, Issue 1, Article 25, 36 pgs.

Bhasin et al., "Pcleavage: an SVM based method for prediction of constitutive preteasome and immunoproteasome cleavage sites in antigenic sequences", Nucleic Acids Research, 2005. vol. 33, Web Server issue, 6 pages.

Panchenko et al., "Combination of Threading Potentials and Sequence Profiles Improves Fold Recognition", Journal of Molecular Biology 296, 2000, 13 pages.

Peters et al., "The Immune Epitope Database and Analysis Resource: From Vison to Blueprint", PLoS Biology, Mar. 2005, vol. 3, Issue 3, 3 pages.

Schmidler et al., "Bayesian Segmentation of Protein Secondary Structure", Journal of Computational Biology, vol. 7, Nos. 1/2, 2000, pp. 233-248.

Freire, "Thermodynamics of protein folding and molecular recognition", IUPAC, Pure & Applied Chemistry, vol. 69, No. 11, 1997, pp. 2253-2261.

Guler, "A Model With an Intrinsic Property of Learning Higher Order Correlations", Neural Networks, vol. 14, 2001, pp. 495-504.

Mamitsuka, "Predicting Peptides That Bind to MHC Molecules Using Supervised Learning of Hidden Markov Models", Proteins: Structure, Function, and Genetics 33, Wiley-Liss, Inc., 1998, pp. 460-474.

Neal, "NIPS (Neural Information Processing Systems)", NIPS 2004 Conference, Dec. 2004.

Nielsen, et al., "Reliable Prediction of T-cell epitopes using neural networks with novel sequence representations", Protein Science, The Protein Society, Cold Spring Harbor Laboratory Press, 2003, pp. 1007-1017.

Swain, et al., "An automated approach to modelling class II MHC alleles and predicting peptide binding", retrieved on Aug. 19, 2009 at <<http://ieeexplore.ieee.org/search/wrapper.jsp?arnumber=974415>>, Bioinformatics and Bioengineering Conference 2001, Proceedings of the IEEE 2nd Int Symposium, 2001, pp. 81-88.

Zhang, et al., "Consistency in structural energetics of protein folding and peptide recognition", Protein Science 6, Cambridge University Press, 1997, pp. 1057-1064.

Espadaler et al., "Prediction of protein-protein interations using distant conservation of sequence patterns and structure relationships", Bioinformatics, vol. 21, No. 16, 2005, pp. 3360-3368.

Waterhouse, "Classification and Regression using Mixtures of Experts", PhD. Thesis, University of Cambridge, 1997, 215 pages.

Bilenko, et al., "Adaptive Duplicate Detection Using Learnable String Similarity Measures", In the Proceedings of the Ninth ACM SIGKDD International Conference on Knowledge Discovery and Data Mining, 2003, pp. 39-48.

Chakrabarti, et al., "Dissecting Protein-Protein Recognition Sites", Wiley-Liss Inc., Proteins: Structure, Function, and Bioinformatics, vol. 47, Issue 3, May 2002, pp. 334-343.

* cited by examiner

CLUSTER MODELING, AND LEARNING CLUSTER SPECIFIC PARAMETERS OF AN ADAPTIVE DOUBLE THREADING MODEL

CROSS-REFERENCE TO RELATED APPLICATIONS

This application is a continuation-in-part (CIP) application of U.S. patent application Ser. No. 11/356,196 filed Feb. 16, 2006, entitled "MOLECULAR INTERACTION PREDICTORS," the entirety of which is incorporated herein by reference.

BACKGROUND

Despite significant progress over the last few years, predicting 3-D protein structure and protein-ligand binding remain difficult problems to solve. Research in this area has focused on complex physics-based models using a large number of particles to describe not only amino acids in proteins, but also the solvent that surrounds them.

One particular example of protein-ligand binding that is of great interest to researchers is interaction between a Major Histocompatibility Complex (MHC) molecule and a peptide. One example of a structural model that can be used to predict peptide-MHC affinity is a threading model. The threading model is based on the premise that proteins fold in a finite number of ways and that change in the short peptide that binds to MHC does not dramatically influence the 3-D binding configuration. Therefore, instead of screening all theoretically possible ways a particular sequence can fold and bind to another peptide to properly choose the sequence's 3-D structure, the protein binding configurations that are already known are used to compute binding energy (or affinity).

Many structures of MHC-peptide binding configurations have been obtained by crystallographers. Since x-ray crystallography reveals that MHC-peptide complexes exhibit a finite number of conformations, the threading approach can be applied to the problem of predicting MHC-peptide binding. The threading approach assumes that energy is additive, but it introduces a simplification that allows estimation of binding energy of a peptide with an MHC molecule whose 3-D configuration of binding with some other peptide is known. In particular, the assumption is that the binding energy is dominated by potentials of pairwise amino acid interactions that occur when the amino acids are in close proximity (e.g., distance smaller than 4.5 Å). Another assumption underlying the threading approach is that the proximity pattern of the peptide in the groove (i.e., MHC binding site) does not change dramatically with the peptide's amino acid content. As the pairwise potentials are assumed to depend only on the amino acids themselves and not on their context in the molecule, the energy becomes a sum of pairwise potentials taken from a symmetric 20×20 matrix of pairwise potentials between amino acids. These parameters are computed based on the amino acid binding physics and there are several published sets derived in different ways.

The MHC-peptide threading procedure utilizes solved MHC-peptide complexes as the threading template, a definition of interacting residues and a pairwise contact potential table. To predict MHC-peptide binding, the query sequence is "threaded" through the various known MHC structures to find the best fit. These structural data files are available, for instance, from the Research Collaboratory for Structural Bioinformatics (RCSB) Protein Data Bank (PDB). The algorithm for the threading model proceeds as follows—given a known structure of an MHC-peptide complex, the contacting MHC residues for each peptide position are determined, the amino acid—amino acid pairwise potentials are used to score interaction of a peptide amino acid at a certain position with all its contacting residues and assuming position independence, the peptide's score is the sum of the amino acid scores.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The subject matter described herein facilitates predicting information about molecular binding (e.g., binding energy, binary binding event, binding probability, etc.). By way of example, amino acid—amino acid interaction potentials and other parameters of a simplified physics-based protein binding model can be learned so as to optimize fit to known binding energy and geometric configuration data. To improve predictions, a mixture model for the model parameters can be used with the mixture component variable treated as hidden. The binding energy can be computed by integrating over the mixing variables—this facilitates adding more parameters into the model in a way that avoids overtraining.

By way of another example, the subject matter includes machine learning techniques that employ known MHC-peptide binding pairs to automatically cluster different MHC proteins and learn cluster-specific parameters of a model (e.g., a mixed adaptive double threading model). The clustering and estimation of binding parameters can be done jointly (e.g., in an Expectation-Maximization fashion). The procedure can be used to learn a separate set of binding parameters as well as a probability distribution over MHC protein content for each cluster. Given a new MHC protein, the posterior distribution over the cluster variable and the expected binding energy can be computed by averaging appropriately the predicted binding energies using different cluster parameters. The mixed adaptive double threading model outperforms the adaptive double threading model, which is a special, single-cluster version of the algorithm, as well as other MHC I energy predictors on the data in Peters et al, PLOS Computational Biology, 2007. Furthermore, the algorithm uses the type and binding parameter grouping to better predict binding for new MHC types (without the use of training data for that particular type, but using the data for other types) compared to what can be accomplished through the use of groupings defined by MHC supertypes.

The following description and the annexed drawings set forth in detail certain illustrative aspects of the subject matter. These aspects are indicative, however, of but a few of the various ways in which the subject matter can be employed and the claimed subject matter is intended to include all such aspects and their equivalents.

DETAILED DESCRIPTION

Figure 1:
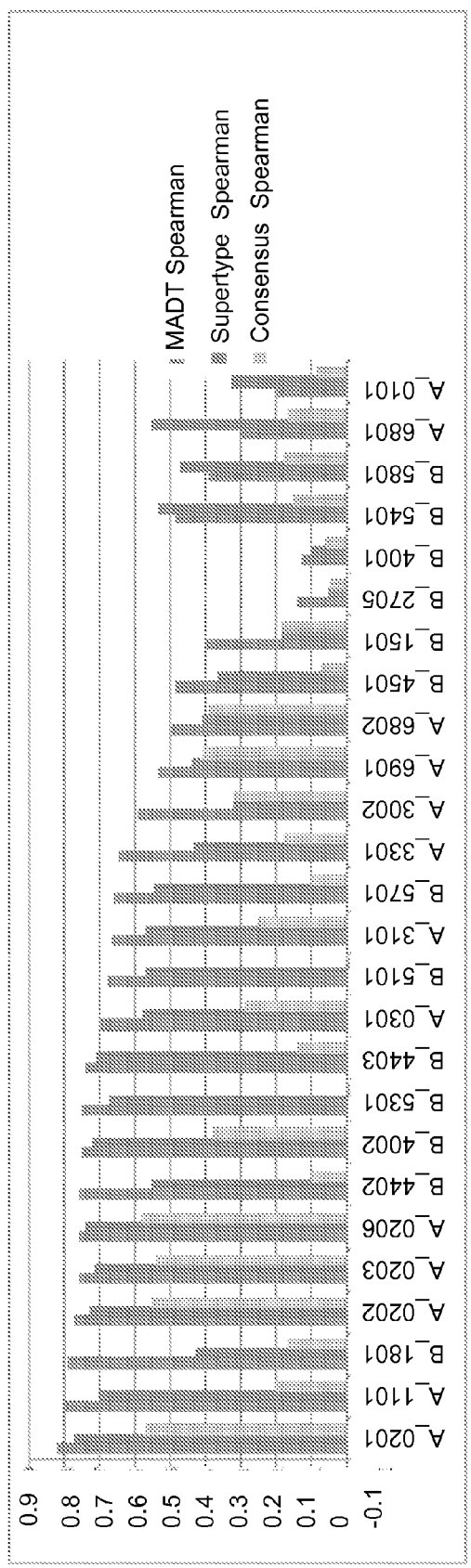
FIG. 1 is a graph showing a comparison of consensus, supertype and the mixed adaptive double threading model-based predictions of peptide binding for different MCH types. Predictors did not use data for the targeted MHC type during training, but did have binding data for other MHC types. The continuous energy prediction performance is shown in terms of Spearman correlation factors.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, well-known structures and devices are shown in block diagram form in order to facilitate describing the claimed subject matter.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, the terms "system," "component," "module," "interface,", "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Artificial intelligence (AI) can be employed to identify a specific context or action, or generate a probability distribution of specific states of a system or behavior of a user without human intervention. Artificial intelligence relies on applying advanced mathematical algorithms—e.g., decision trees, neural networks, regression analysis, cluster analysis, genetic algorithm, and reinforced learning—to a set of available data (information) on the system or user.

Although the subject matter described herein may be described in the context of MHC-peptide binding and adaptive double threading models, the subject matter is not limited to these particular embodiments. Rather, the techniques described herein can be applied to any suitable type of molecular binding and any suitable models.

By way of example, MHC molecules play important roles in the workings of the human immune system. The specificity of MHC binding to short peptide samples from cellular as well as pathogenic proteins (e.g., epitopes) has been found to correlate with disease outcome and pathogen or cancer evolution. It is also widely believed to have important consequences to rational vaccine design. The diversity of the MHC molecules is considerably higher than the norm, leading to significant differences in the peptide binding specificity among different individuals.

The interaction between an MHC molecule and a peptide can be characterized by a binding free energy. The lower the binding free energy, the greater the affinity between the two proteins. The binding free energy is the difference between free energy of bound and unbound states. The binding energy for an MHC-peptide complex can be directly measured by competition experiments with a standard peptide. Typically, it is expressed as the ratio between half-maximal inhibitory concentration (IC50) of the standard peptide to that of a test peptide. In the context of MHC-peptide binding, IC50 is the concentration of the test peptide required to inhibit binding of the standard peptide to MHC by 50%. The result of such experiments is a set of relative binding energies (negative logarithms of the relative concentrations) for different MHC-peptide combinations.

By way of example, a binding energy model can be based on the geometry of MHC-peptide complexes, such as one motivated by the threading approach (see O. Schueler-Furman, Y. Altuvia, A. Sette and H. Margalit, "Structure-based prediction of binding peptides to MHC class I molecules: Application to a broad range of MHC alleles," Protein Science (2000) 9:1838-1846). In general, threading aims at evaluating the compatibility of a certain protein sequence with a certain protein structure. The sequence is threaded onto the structure, and a list of contacting amino acid pairs is extracted based on contacting residue positions (defined as residues in close proximity, e.g., those that have at least one pair of atoms less than 4.5 Å apart). In order to allow estimation of the binding energy of any peptide with an MHC molecule whose structure in complex with some other peptide is known, the proximity pattern of the peptide in the groove is assumed not to change dramatically with the peptide's sequence.

By way of another example, as shown in N. Jojic, M. Reyes-Gomez, D. Heckerman, C. Kadie, and O. Schueler-Furman, "Learning MHC I Peptide Binding," Bioinformatics 2006, 22: e227-e235, the threading model can be augmented by including learnable parameters. Assuming that energy is additive, and that the pairwise potentials depend only on the amino acids themselves (and not on their context in the molecule) the energy becomes a sum of pairwise potentials taken from a symmetric 20×20 matrix of pairwise potentials between amino acids. These parameters can be computed based on the amino acid binding physics or from statistical analyses of amino acid pair contact preferences in large sets of available protein structures.

Several sets of pairwise potentials have been described in the literature, each derived in a different way. The choice of pairwise potential matrix can dramatically alter performance of the energy predictor. Estimating these parameters from training data leads to the better performance on the test set compared to using a previously published, rationally derived potential matrix. One potential explanation for this result is the possible specialization to the class of molecules under consideration. However, the model still preserves its physics basis, as for example, the learned weights tend to reveal contact amino acids.

In the adaptive double threading model of MHC I—peptide binding (see Jojic, et al. above), the binding energy can be estimated as:

$$E(s, e) \approx \sum_i \sum_j w_{i,j} \phi_{s_i,e_j} h(d_{i,j}), \quad (1)$$

where learnable MHC-specific weights $w_{i,j}$ and a trainable soft threshold function h provide added parameters that correct for the drastic approximations in the original threading approach (see O. Schueler-Furman, et al. above). In the above equation, s denotes the MHC molecule's amino acid sequence indexed by i, e denotes the peptide (e.g., epitope) sequence indexed by j and $\phi_{s_i,e_j}$ are learnable contact potentials. The distances $d_{i,j}$ are computed based on the crystal structure of a binding configuration of sequence s and some arbitrary reference peptide different from e or the crystal structure of a completely different MHC-peptide pair. This approach is possible because there is a high degree of similarity among the crystal structures of different MHC-peptide pairs. Alternatively, consensus structure can be computed given multiple binding configurations and the selection of the optimal binding configuration for each peptide e from a selection of crystal structures can be computed or from other MHC types' structures.

During binding, only a small fraction of the MHC molecules' amino acids (indexed by i in equation (1)) are in contact with the peptide. One example of a soft step function that can be used in equation (1) is:

$$h(d) = \frac{1}{1 + e^{-A(d - d_{thr})}}, \quad (2)$$

where the threshold parameter $d_{thr}$ and the step softness A are estimated together with the contact potentials $\phi_{s_i,e_j}$ and weights $w_{i,j}$. Only a small number of amino acids in the molecule are close enough to the peptide to lead to nonzero values of h, and thus, the "soft" groove is also small. As explained above, the adaptive soft step function h and the addition of the weights w are meant to absorb the errors of the original model's assumptions. The predictions of the original threading approach can be thought of as equation (1) with all weights w set to one, and the threshold function h set to a hard step with a threshold decided upon in advance. For instance, a hard step function h(d) with a threshold distance $d_{thr}$ of <4.5 Å such that:

$$h(d) = \begin{cases} 1, & d \leq d_{thr} \\ 0, & d > d_{thr} \end{cases}. \quad (3)$$

The basic idea behind the adaptive threading approach is that, even though the structure information d is inferred from a known binding configuration of a particular peptide-MHC I combination, substituting a different peptide of the same length (or even another MHC molecule) in equation (1) would still lead to a reasonable estimate of the binding energy for the new MHC-peptide combination. This is because the relative positions and the basic chemistry of the amino acid—amino acid interactions are fixed. Even the light changes over different geometries of peptide-groove configurations (indexed by m) have a small (though measurable) effect on the accuracy of the model. As shown in Jojic, et al., this assumption holds well for MHC I binding energy prediction.

As is also shown in Jojic, et al., the parameters of the above model can be estimated so that the error of approximation is minimized on the training set, and the model's predictive power then can be tested on a separate test set. When the training data sets are too small, sparsity priors on w and cross-validation are used to avoid overtraining. However, multiple different MHC types can be trained together as they can share some or all parameters. Parameter sharing leads to a negligible drop in performance, while the main benefit is not merely avoidance of overtraining, but the ability to generalize the predictions to new MHC alleles for which little or no binding or epitope data is available.

In principle, a fully physics-based model would need no further improvement. The adaptive-double threading model, however, borrows from physics but remains simplified and requires training the parameters to fit the data. These parameters help the model specialize to the class of proteins (e.g., MHC proteins), which is the reason why this model outperforms the traditional threading approaches (which were fully rational, and aimed at being applicable to all proteins). By way of example, to further enable the model to specialize to subclasses of proteins (such as MHC molecules, which come in hundreds if not thousands of variants), a mixture (or cluster or class) variable c can be added to a model. For instance, a cluster variable can be added to an adaptive threading model:

$$E(s, e, c) \approx \sum_i \sum_j w_{i,j}^c \phi_{s_i,e_j}^c h(d_{i,j}), \quad (4)$$

The predictions can be conditioned on this variable or in terms of a probability distribution over the binding energy:

$$p(E \mid s, e, c) = N\left(E; \sum_i \sum_j w_{i,j}^c \phi_{s_i,e_j}^c h(d_{i,j}), \sigma^2\right), \quad (5)$$

where $N(x; \mu, \sigma^2)$ denotes a Gaussian distribution over x, with mean $\mu$ and variance $\sigma^2$.

If it is assumed that each cluster c tends to be responsible for a class of MHC types m (probably with some level of similarity in their sequence content $s^m$), a probability distribution function p(m|c) over type as a symbolic variable, or over the MHC sequence $s^m$ using, for instance, $p(s|c) = \Pi_i p(s_i|c)$, with each $p(s_i|c)$ being a multinomial distribution over the 20 amino acids can be introduced (this corresponds to the usual position-specific scoring matrices models used in bioinformatics). More complex models p(s|c) can be used. Prior distribution over clusters p(c) completes the model, which defines the following joint distribution over the MHC sequence and the binding energy for a given peptide e:

$$p(E, m, c|e) = p(E|s^m, e, c) * p(m|c) p(c). \quad (6)$$

Examples of the binding data triples ($E^t, e^t, m^t$) can be used to learn the parameters $w^c$ and $\phi^c$ by employing Expectation-Maximization (EM), which alternates cluster inference (E step):

$$p(c = k \mid E, m, e) = \frac{p(E, s^m, c = k \mid e)}{\sum_c p(E, s^m, c \mid e)}, \quad (7)$$

with the optimization of cluster parameters (M step):

$$(w^c, \phi^c) = \operatorname{argmin}_{w^c, \phi^c} \quad (8)$$

$$\sum_i p(c \mid E^t, m^t, e^t) \left( E^t - \sum_i \sum_j w^c_{i,j} \phi^c_{s^{m^t}_i, e^t_j} h(d_{i,j}) \right)^2,$$

the noise variance (also M step), $$\sigma^2 = \frac{1}{T} \sum_t \sum_c p(c \mid E^t, m^t, e^t) \left( E^t - \sum_i \sum_j w^c_{i,j} \phi^c_{s^{m^t}_i, e^t_j} h(d_{i,j}) \right)^2. \quad (9)$$

and the distribution p(c,m)

$$p(c, m) \propto \sum_i [m^t = m] p(c \mid E^t, m^t, e^t), \quad (10)$$

with [ ] denoting the indicator function. As in the original adaptive double threading model, the bilinear dependence of the energy estimate on the model parameters is used to solve for the cluster parameters in the M step by iterating optimization with respect to $w^c$ parameters with the optimization with respect to $\phi^c$. The noise variance $\sigma^2$ can be updated as it influences the softness of the assignment of the clusters in the E step.

As opposed to the learning stage (which can utilize data in triplets (E,m,e)), the energy prediction can use the MHC-peptide pairs (m,e) as the inputs and the probability model above to compute the expected energy $\bar{E}$ as:

$$\bar{E} = \sum_c p(c \mid m) \sum_i \sum_j w^c_{i,j} \phi^c_{s^m_i, e_j} h(d_{i,j}), \quad (11)$$

where $$p(c \mid m) \propto p(c, m), \quad (12)$$

since there is no observation of energy E to influence the inference of class c. This way of estimating the binding energy essentially uses the individual basic double threading models indexed with c to define a subspace in which the prediction lies. The prediction is a linear combination of the basis models with weights defined by p(c|m). The probabilistic relationship between class c and the type m serves as a soft clustering of MHC types into something akin to supertypes (clusters of MHC molecules with similar binding targets that have been previously observed by immunologists). The clustering described herein provides better results in terms of generalizing the binding predictions than previously defined supertypes.

The model described above (referred to as the mixed adaptive double threading model (MADT)) was trained on the comprehensive data set published in B. Peters, HH Bui, S. Frankild, M. Nielsen, C. Lundegaard, "A Community Resource Benchmarking Predictions of Peptide Binding to MHC-I Molecules," PLoS Computational Biology (2006), in press, DOI: 10.1371/journal.pcbi.0020065.eor, and compared with the basic adaptive double threading model (see Jojic, et al.) and other methods. The data set contains 29,371 binding energies for different MHC-peptide pairs and spans 35 different MHC types. The basic adaptive double threading (ADT) model, which is a special, single-cluster, case of the MADT, was very close in performance to the best of the models tested by Peters et al. In terms of classifying test peptides into good binders vs. bad binders, the ADT performed slightly worse than the best of the models in Peters et al. (an AUC of 0.88 vs. 0.89). The MADT with 10 clusters with an AUC of 0.9 was slightly better than all methods previously tested on this dataset.

One possible explanation for the improved performance of the MADT is that it is due to an increased number of model parameters, since each cluster has a separate set of parameters. However, despite the increased number of parameters, the MADT still has strong generalization capabilities. For example, in cases of MHC molecules for which the state of the art in Peters et al. outperforms the MADT, there were on average 1093 peptides per MHC type in the training set. In the instances that the MADT outperforms the other methods, there were on average only 569 peptides per MHC type in the training set.

As discussed above, clustering MHC types into groups that share a binding model is similar in spirit to the idea of MHC supertypes. It is also in the spirit of establishing a similarity measure over proteins that capture binding similarities as was proposed in a different context in Hertz T and Yanover C., "PepDist: A New Framework for Protein-Peptide Binding Prediction Based on Learning Peptide Distance Functions," BMC Bioinformatics, 2006 Mar. 20; 7, Suppl 1:S3. However, the MADT model establishes a similarity measure among the MHC molecules and not the peptide targets. The MADT model in its basic and mixed versions uses both the MHC sequence and the peptide sequence to predict binding, and the additional clustering of the binding models as well as types is meant to absorb errors in modeling, as in principle, the sequence content should be enough to predict binding without grouping of MHC types. For the ADT model, this grouping is necessary to break the types into groups which can indeed share a binding model despite the simplification. Each of these groups may have some unique aspects of their binding configuration that make the best threading model parameters slightly different. The experiments indicate, however, that the separation into groups is soft.

One way to compare the traditional supertype classification with the one learned by the MADT model is to compare the two classifications on the generalization task: prediction of MHC-peptide binding using only the training data for other MHC types, and not the type tested. In this generalization experiment, for each of the 35 MHC types in the dataset, the ADT model was trained using only the binding data for the remaining 34 MHC types. Then for all peptides in the test set two different baseline energy predictions were computed for the targeted MHC type. The first one (consensus) averages predictions over all 34 MHC types other than the target type, while the second baseline prediction (supertype) averages only over the MHC types that belong to the same supertype as the target type (using the supertype classification at the LANL HIV web site). The latter prediction is somewhat similar to the mixing of the model described herein (with specific pre-defined distributions p(m|c)). Note that both of these techniques use no information about the target MHC except its supertype identity in the latter case.

Figure 2:
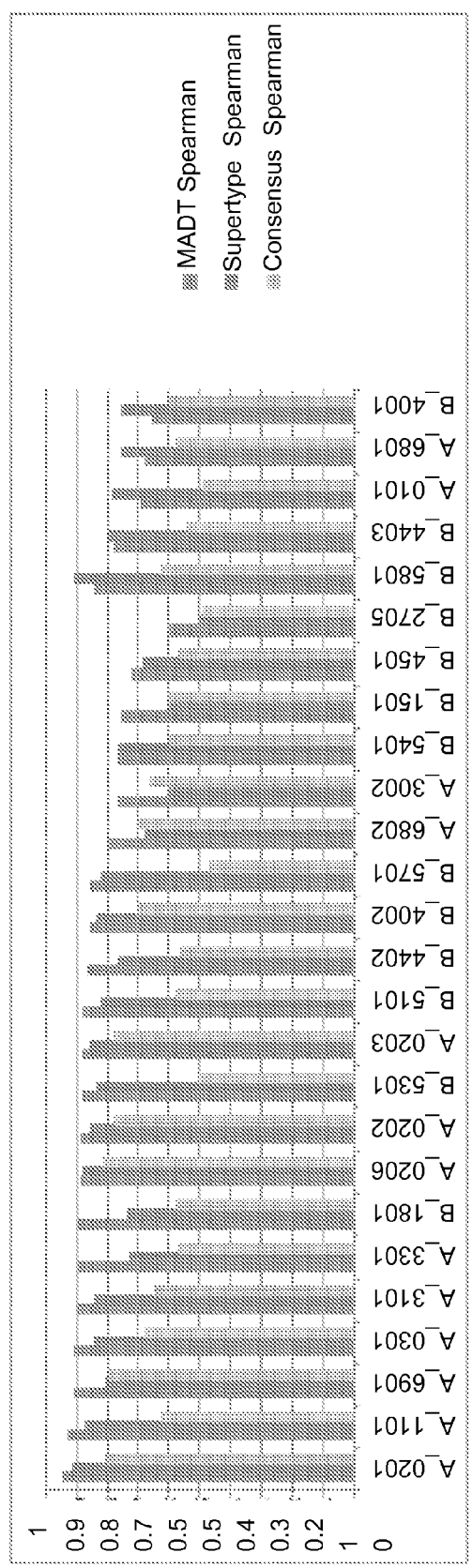
FIG. 2 is a graph showing binders vs. nonbinders in terms of the area under an ROC curve (AUC).

These two baseline predictions were compared with the prediction of the MADT model trained on the same training data (using all MHC-peptide pairs but the ones related to the target MHC type). In equation (10), the sequence $s^m$ of the target type m is used and to obtain the necessary distribution p(c|m'), the closest type m' in terms of the sequence content is found and p(c|m') is used. Alternatively, a sequence pdf p(s|c) can be used rather than the type pdf p(m|c) in the MADT during training, thus making it possible to make the inference p(c|s) directly from the sequence s without searching for the closest type m'. The consensus prediction is a straw man prediction that focuses on similarities of binding across all MHC types and ignores the differences. The supertype prediction does the same but only within each supertype, as it was previously argued that most differences in binding can be explained by these supertypes. The supertype-based predictions are, as expected, much better than the consensus predictions. The MADT prediction is sequence based, and outperforms the supertype-based predictions for 85% of the types (see FIGS. 1 and 2).

Figure 3:
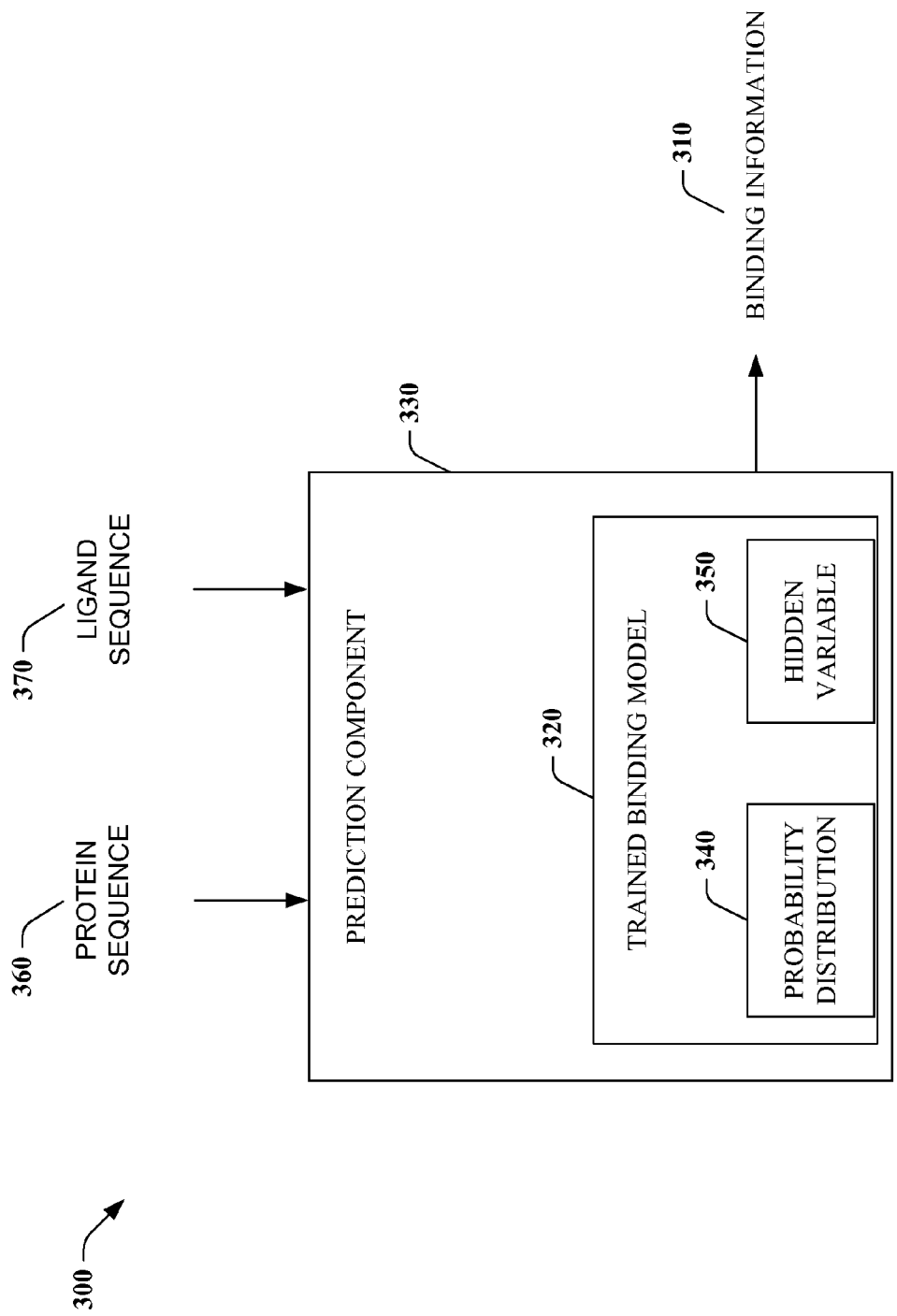
FIG. 3 is a block diagram of one example of a system for predicting binding information relating to the binding of a protein and a ligand.

FIG. 3 schematically illustrates one example of a system 300 for predicting binding information 310 (e.g., binding energy, binary binding event such as whether a peptide is a binder or is not a binder or a probability) relating to the binding of a protein (e.g., an MHC class I molecule or a synthetic molecule) and a ligand (e.g., a peptide of about 8-11 amino acids in length). The system 300 can be, for instance, a computer executed system such as one stored on computer-readable media. The system 300 can include a trained binding model 320 and a prediction component 330. The trained binding model 320 can include a probability distribution 340 and a hidden variable 350 that represents a cluster of protein sequences. The prediction component 330 can be configured to predict the binding information 310 by employing information about the protein's sequence 360, the ligand's sequence 370 and the trained binding model 320. The system 300 can be implemented by software or combinations of software and hardware and can be the same process executing on a single or a plurality of microprocessors or multiple processes executing on a single or a plurality of microprocessors.

The trained binding model 320 can be any suitable binding model such as those described above (e.g., a mixed adaptive double threading model). The trained binding model 320 can include any suitable parameters (e.g., MHC-specific weights, learnable contact potentials, learnable soft-step function). For instance, a learnable soft-step function given by:

$$h(d) = \frac{1}{1 + e^{-A(d-d_{thr})}}$$

By way of example, the trained binding model 320 can be given by:

$$\bar{E} = \sum_c p(c|m) \sum_i \sum_j w^c_{i,j} \phi^{c_m}_{s^m_i, e_j} h(d_{i,j}),$$

where $p(c|m) \propto p(c,m).$

One can also make the binding energy a function of hidden variables $l_1(MHC), \ldots, l_L(MHC)$, which represent independent supertypes. In the most general case, in which we include both c and the l's in the model, we have $$\bar{E} = \sum_c p(c|m) \sum_i \sum_j w^c_{i,j} \phi^{c_m}_{s^m_i, e_j} h(d_{i,j}) + \sum_k \alpha_k l_k(MHC)$$

where $l_k(MHC)$ can be a logistic regression of the features of the MHC. Those practiced in the art will recognize that the generalized EM algorithm used to learn the parameters of the original model can be extended to learn the parameters of the logistic regression as well as $\alpha_k$.

The systems described above can be implemented in whole or in part by electromagnetic signals. These manufactured signals can be of any suitable type and can be conveyed on any type of network. For instance, the systems can be implemented by electronic signals propagating on electronic networks, such as the Internet. Wireless communications techniques and infrastructures also can be utilized to implement the systems.

Figure 4:
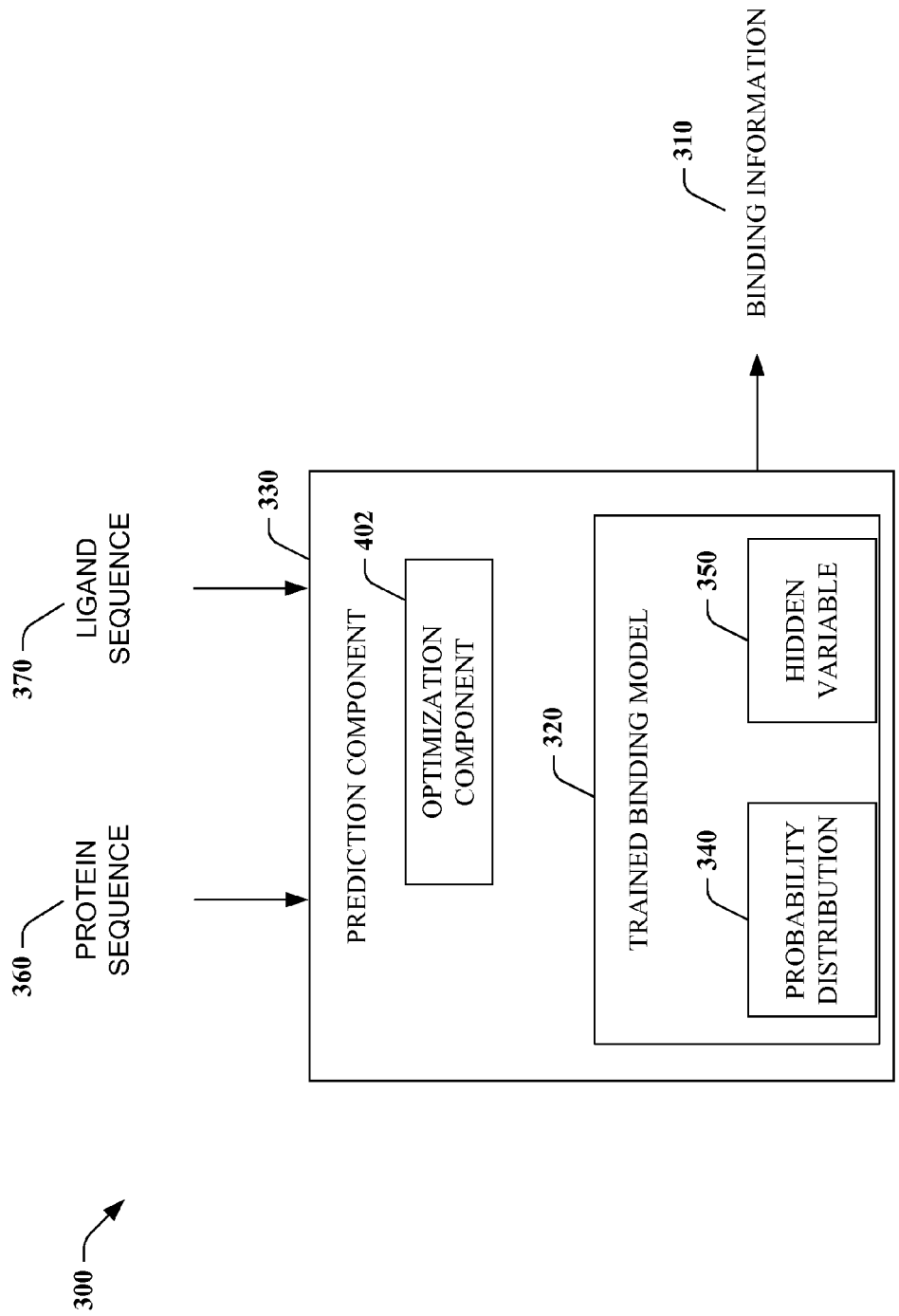
FIG. 4—is a block diagram of an embodiment of a system for predicting binding information relating to the binding of a protein and a ligand that employs an optimization component.

FIG. 4 illustrates an embodiment of the system 300 that includes an optional optimization component 402. The optimization component 402 can be employed in connection with making determinations or inferences regarding optimization decisions and the like. The optimization component 402 can employ a probabilistic-based or statistical-based approach, for example, in connection with making determinations or inferences. The inferences can be based in part upon explicit training of classifier(s) (not shown) before employing the system 300, or implicit training based at least upon previous, or current actions, commands, instructions, and the like during use of the system.

The optimization component 402 can employ one of numerous methodologies for learning from data and then drawing inferences from the models so constructed (e.g., Hidden Markov Models (HMMs) and related prototypical dependency models, more general probabilistic graphical models, such as Bayesian networks, e.g., created by structure search using a Bayesian model score or approximation, linear classifiers, such as support vector machines (SVMs), non-linear classifiers, such as methods referred to as "neural network" methodologies, fuzzy logic methodologies, and other approaches that perform data fusion, etc.) in accordance with implementing various automated aspects described herein.

Methods also include methods for capture of logical relationships such as theorem provers or more heuristic rule-based expert systems. Inferences derived from such learned or manually constructed models can be employed in optimization techniques, such as linear and non-linear programming, that seek to maximize some objective function.

The optimization component 402, can take into consideration historical data, and data about current context. Policies can be employed that consider including consideration of the cost of making an incorrect determination or inference versus benefit of making a correct determination or inference. Accordingly, an expected-utility-based analysis can be used to provide inputs or hints to other components or for taking automated action directly. Ranking and confidence measures can be calculated and employed in connection with such analysis.

It should be appreciated that optimization is dynamic and policies selected and implemented will vary as a function of numerous parameters; and thus the optimization component 402 is adaptive.

Figure 5:
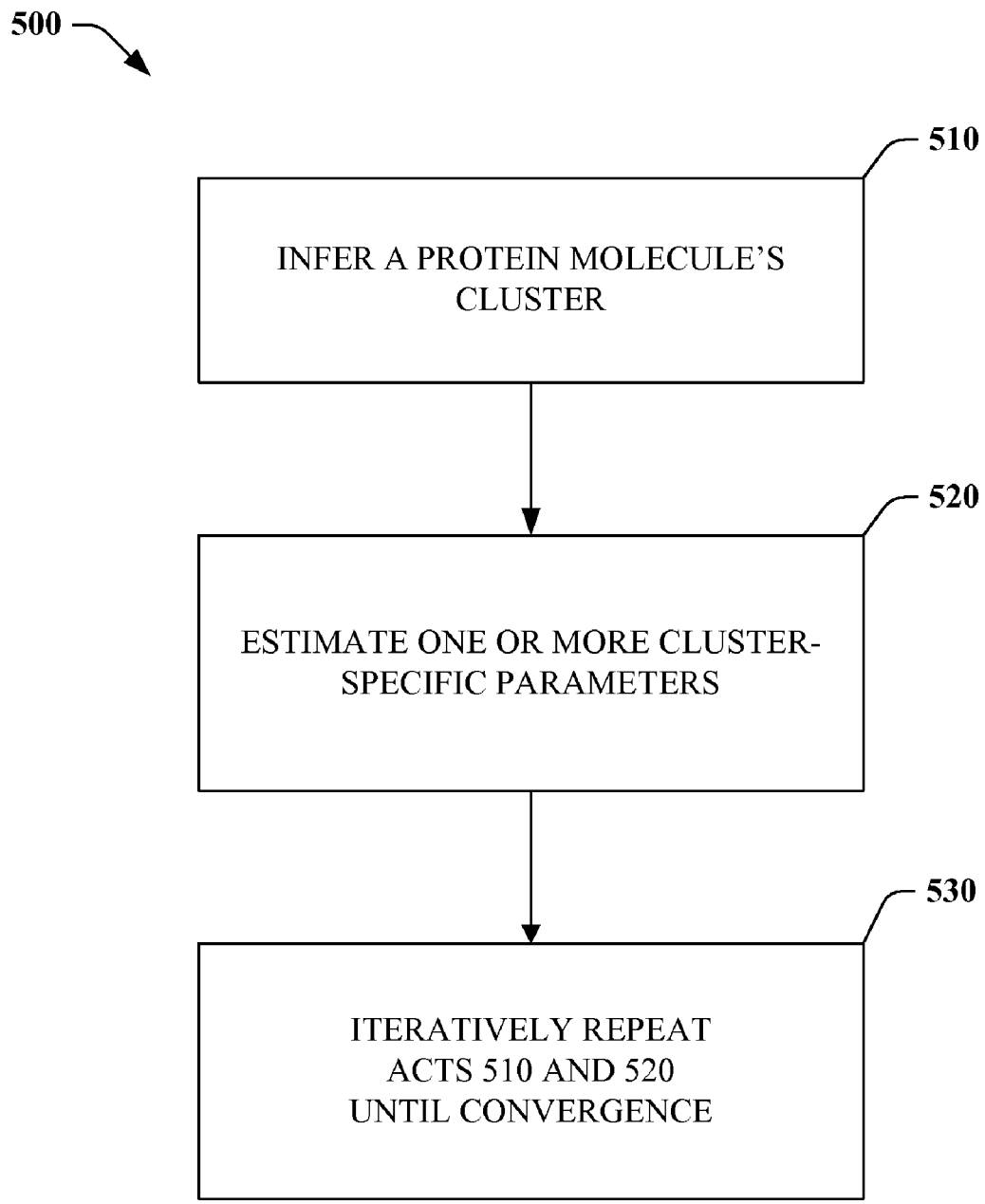
FIG. 5 is a flow diagram of one example of a method of generating a binding predictor.

FIG. 5 is a flow diagram of one example of a method 500 of generating a binding predictor. The method 500 can be encoded by computer-executable instructions stored on computer-readable media. The binding predictor can be any suitable predictor such as those described above (e.g., a predictor to predict the binding of an MHC molecule and a peptide from about 8-11 amino acids in length, a mixed adaptive double threading predictor) and can predict any suitable binding information such as those described above (e.g., binding energy, binary binding event, binding probability). At step 510, a protein molecule's (e.g., an MHC molecule's) cluster is inferred from training data. At step 520, one or more cluster-specific parameters of the binding predictor are estimated from the training data. Steps 510 and 520 are iteratively repeated until convergence as shown in step 530.

The steps 510 and 520 of the method 500 can be accomplished in any suitable manner such as those described above. For instance, the step of inferring the protein molecule's cluster 510 can be accomplished by computing:

$$p(c = k \mid E, m, e) = \frac{p(E, s^m, c = k \mid e)}{\sum_c p(E, s^m, c \mid e)}.$$

By way of another example, the step of iteratively re-inferring the protein molecule's cluster and re-estimating the one or more cluster-specific parameters of the binding predictor 530 can be accomplished using stochastic gradient descent. By way of yet another example, the step of estimating the one or more cluster-specific parameters of the binding predictor 520 can include updating a noise variance (e.g., equation (9) above).

The methods can be implemented by computer-executable instructions stored on one or more computer-readable media or conveyed by a signal of any suitable type. The methods can be implemented at least in part manually. The steps of the methods can be implemented by software or combinations of software and hardware and in any of the ways described above. The computer-executable instructions can be the same process executing on a single or a plurality of microprocessors or multiple processes executing on a single or a plurality of microprocessors. The methods can be repeated any number of times as needed and the steps of the methods can be performed in any suitable order.

The subject matter described herein can operate in the general context of computer-executable instructions, such as program modules, executed by one or more components. Generally, program modules include routines, programs, objects, data structures, etc., that perform particular tasks or implement particular abstract data types. Typically, the functionality of the program modules can be combined or distributed as desired. Although the description above relates generally to computer-executable instructions of a computer program that runs on a computer and/or computers, the user interfaces, methods and systems also can be implemented in combination with other program modules. Generally, program modules include routines, programs, components, data structures, etc. that perform particular tasks and/or implement particular abstract data types.

Moreover, the subject matter described herein can be practiced with most any suitable computer system configurations, including single-processor or multiprocessor computer systems, mini-computing devices, mainframe computers, personal computers, stand-alone computers, hand-held computing devices, wearable computing devices, microprocessor-based or programmable consumer electronics, and the like as well as distributed computing environments in which tasks are performed by remote processing devices that are linked through a communications network. In a distributed computing environment, program modules can be located in both local and remote memory storage devices. The methods and systems described herein can be embodied on a computer-readable medium having computer-executable instructions as well as signals (e.g., electronic signals) manufactured to transmit such information, for instance, on a network.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing some of the claims.

It is, of course, not possible to describe every conceivable combination of components or methodologies that fall within the claimed subject matter, and many further combinations and permutations of the subject matter are possible. While a particular feature may have been disclosed with respect to only one of several implementations, such feature can be combined with one or more other features of the other implementations of the subject matter as may be desired and advantageous for any given or particular application.

Moreover, it is to be appreciated that various aspects as described herein can be implemented on portable computing devices (e.g., field medical device), and other aspects can be implemented across distributed computing platforms (e.g., remote medicine, or research applications). Likewise, various aspects as described herein can be implemented as a set of services (e.g., modeling, predicting, analytics, etc.).

Figure 6:
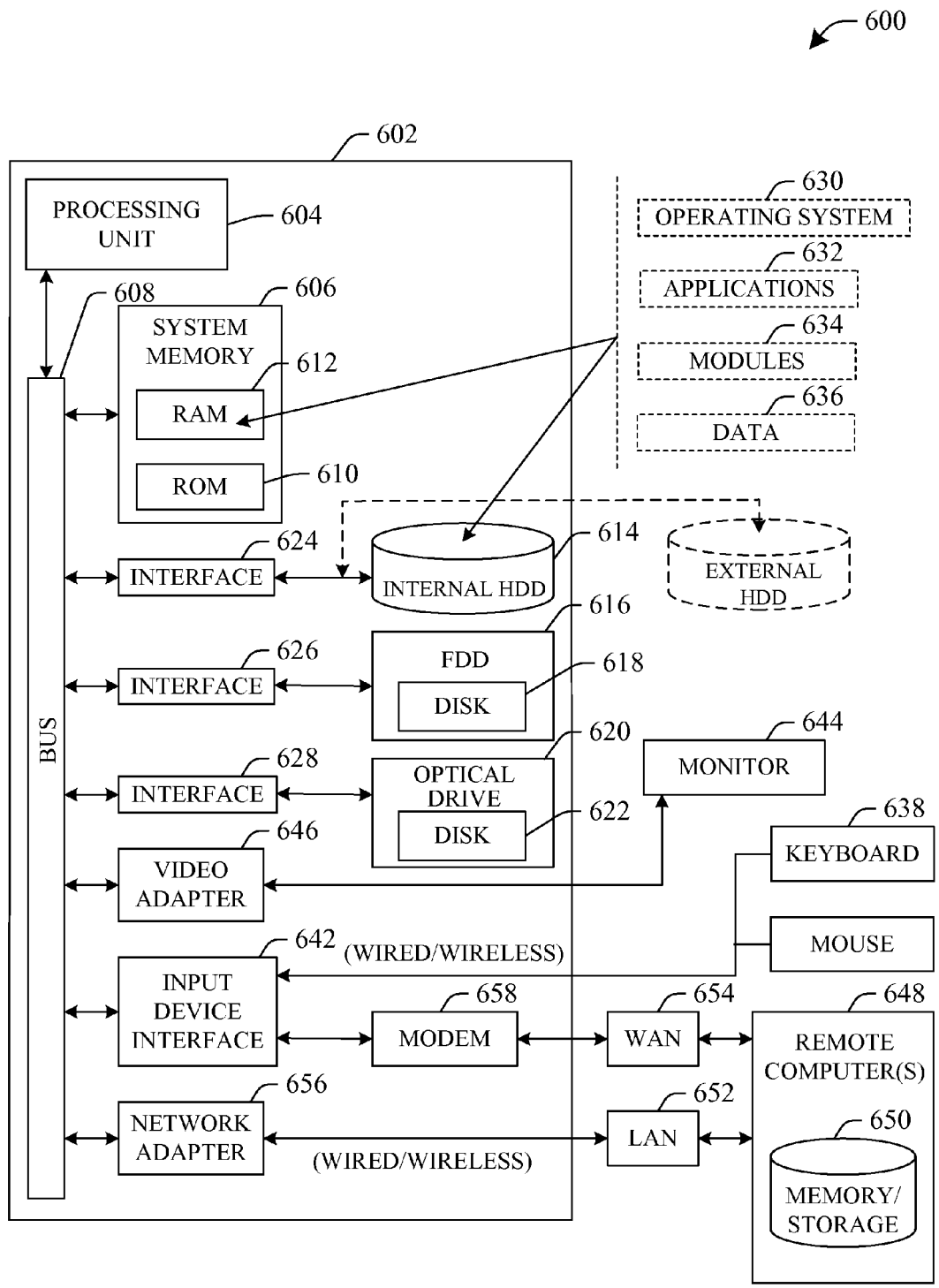
FIG. 6 is an example computing environment in accordance with various aspects described herein.

FIG. 6 illustrates a block diagram of a computer operable to execute the disclosed architecture. In order to provide additional context for various aspects of the subject specification, FIG. 6 and the following discussion are intended to provide a brief, general description of a suitable computing environment 600 in which the various aspects of the specification can be implemented. While the specification has been described above in the general context of computer-executable instructions that may run on one or more computers, those skilled in the art will recognize that the specification also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the specification may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

More particularly, and referring to FIG. 6, an example environment 600 for implementing various aspects as described in the specification includes a computer 602, the computer 602 including a processing unit 604, a system memory 606 and a system bus 608. The system bus 608 couples system components including, but not limited to, the system memory 606 to the processing unit 604. The processing unit 604 can be any of various commercially available processors. Dual microprocessors and other multi-processor architectures may also be employed as the processing unit 604.

The system bus 608 can be any of several types of bus structure that may further interconnect to a memory bus (with or without a memory controller), a peripheral bus, and a local bus using any of a variety of commercially available bus architectures. The system memory 606 includes read-only memory (ROM) 610 and random access memory (RAM) 612. A basic input/output system (BIOS) is stored in a nonvolatile memory 610 such as ROM, EPROM, EEPROM, which BIOS contains the basic routines that help to transfer information between elements within the computer 602, such as during start-up. The RAM 612 can also include a high-speed RAM such as static RAM for caching data.

The computer 602 further includes an internal hard disk drive (HDD) 614 (e.g., EIDE, SATA), which internal hard disk drive 614 may also be configured for external use in a suitable chassis (not shown), a magnetic floppy disk drive (FDD) 616, (e.g., to read from or write to a removable diskette 618) and an optical disk drive 620, (e.g., reading a CD-ROM disk 622 or, to read from or write to other high capacity optical media such as the DVD). The hard disk drive 614, magnetic disk drive 616 and optical disk drive 620 can be connected to the system bus 608 by a hard disk drive interface 624, a magnetic disk drive interface 626 and an optical drive interface 628, respectively. The interface 624 for external drive implementations includes at least one or both of Universal Serial Bus (USB) and IEEE 1394 interface technologies. Other external drive connection technologies are within contemplation of the subject specification.

The drives and their associated computer-readable media provide nonvolatile storage of data, data structures, computer-executable instructions, and so forth. For the computer 602, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the example operating environment, and further, that any such media may contain computer-executable instructions for performing the methods of the specification.

A number of program modules can be stored in the drives and RAM 612, including an operating system 630, one or more application programs 632, other program modules 634 and program data 636. All or portions of the operating system, applications, modules, and/or data can also be cached in the RAM 612. It is appreciated that the specification can be implemented with various commercially available operating systems or combinations of operating systems.

A user can enter commands and information into the computer 602 through one or more wired/wireless input devices, e.g., a keyboard 638 and a pointing device, such as a mouse 640. Other input devices (not shown) may include a microphone, an IR remote control, a joystick, a game pad, a stylus pen, touch screen, or the like. These and other input devices are often connected to the processing unit 604 through an input device interface 642 that is coupled to the system bus 608, but can be connected by other interfaces, such as a parallel port, an IEEE 1394 serial port, a game port, a USB port, an IR interface, etc.

A monitor 644 or other type of display device is also connected to the system bus 608 via an interface, such as a video adapter 646. In addition to the monitor 644, a computer typically includes other peripheral output devices (not shown), such as speakers, printers, etc.

The computer 602 may operate in a networked environment using logical connections via wired and/or wireless communications to one or more remote computers, such as a remote computer(s) 648. The remote computer(s) 648 can be a workstation, a server computer, a router, a personal computer, portable computer, microprocessor-based entertainment appliance, a peer device or other common network node, and typically includes many or all of the elements described relative to the computer 602, although, for purposes of brevity, only a memory/storage device 650 is illustrated. The logical connections depicted include wired/wireless connectivity to a local area network (LAN) 652 and/or larger networks, e.g., a wide area network (WAN) 654. Such LAN and WAN networking environments are commonplace in offices and companies, and facilitate enterprise-wide computer networks, such as intranets, all of which may connect to a global communications network, e.g., the Internet.

When used in a LAN networking environment, the computer 602 is connected to the local network 652 through a wired and/or wireless communication network interface or adapter 656. The adapter 656 may facilitate wired or wireless communication to the LAN 652, which may also include a wireless access point disposed thereon for communicating with the wireless adapter 656.

When used in a WAN networking environment, the computer 602 can include a modem 658, or is connected to a communications server on the WAN 654, or has other means for establishing communications over the WAN 454, such as by way of the Internet. The modem 658, which can be internal or external and a wired or wireless device, is connected to the system bus 608 via the serial port interface 642. In a networked environment, program modules depicted relative to the computer 602, or portions thereof, can be stored in the remote memory/storage device 650. It will be appreciated that the network connections shown are example and other means of establishing a communications link between the computers can be used.

The computer 602 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for generating a binding predictor executed on a processing unit, the method comprising:
   training data based on using a compatibility of a model;
   inferring a class for a protein from the training data;
   estimating one or more parameters of the binding predictor from the training data to minimize an error of approximation on the training data, each of the one or more parameters pertaining to a class of major histocompatibility complex (MHC) types;
   grouping the one or more parameters pertaining to the class of MHC types to predict binding based on the training data of other MHC types;
      iteratively re-inferring the class for the protein and re-estimating the one or more parameters pertaining to the class until converging to a value of about one; and
   using data of the other MHC types and the grouping of the one or more parameters to predict binding for new MHC types.

2. The method of claim 1, wherein the act of inferring the class for the protein comprises computing:

$$p(c = k \mid E, m, e) = \frac{p(E, s^m, c = k \mid e)}{\sum_c p(E, s^m, c \mid e)}$$

wherein p represents a prediction, c represents a mixture, a cluster, or a class variable, k is equivalent to the variable c, E represents energy, m represents a type, e represents a peptide sequence, and s represents the MHC molecule's amino acid sequence.

3. The method of claim 1, wherein the act of iteratively re-inferring the class for the protein and re-estimating the one or more parameters pertaining to the class of the binding predictor comprises employing a stochastic gradient descent.

4. The method of claim 1, wherein the act of estimating the one or more parameters pertaining to the class of the binding predictor comprises updating a noise variance.

5. The method of claim 1, wherein the protein molecule is an MHC molecule.

6. The method of claim 1, comprising instructions that learn amino acid—amino acid interaction potentials and other parameters of a simplified physics-based protein binding model to facilitate optimizing fit to known binding energy and geometric configuration data.

7. The method of claim 1, comprising instructions that employ a mixture model for model parameters with a mixture component variable treated as a hidden variable to facilitate improving predictions.

8. The method of claim 1, comprising instructions that employ machine learning techniques that utilize known MHC-peptide binding pairs to automatically cluster different MHC proteins and learn parameters pertaining to the class of a mixed adaptive double threading model.

9. A memory storage device configured with executable instructions that, when executed by one or more processors, configure the one or more processors to perform acts comprising:
   training data based on using a compatibility of a model;
   inferring a class for a protein from the training data;
   estimating one or more parameters of the binding predictor from the training data to minimize an error of approximation on the training data, each of the one or more parameters pertaining to a class of major histocompatibility complex (MHC) types;
   grouping the one or more parameters pertaining to the class of MHC types to predict binding based on the training data of other MHC types;
      iteratively re-inferring the class for the protein and re-estimating the one or more parameters pertaining to the class until converging to a value of about one; and
   using data of the other MHC types and the grouping of the one or more parameters to predict binding for new MHC types.

10. The memory storage device as recited in claim 9, wherein iteratively re-inferring the class for the protein and re-estimating the one or more parameters pertaining to the class of the binding predictor comprises employing a stochastic gradient descent.

11. The memory storage device as recited in claim 9, wherein estimating the one or more parameters pertaining to the class of the binding predictor comprises updating a noise variance.

12. The memory storage device as recited in claim 9, the acts further comprising learning amino acid—amino acid interaction potentials and other parameters of a simplified physics-based protein binding model to facilitate optimizing fit to known binding energy and geometric configuration data.

13. The memory storage device as recited in claim 9, the acts further comprising employing a mixture model for model parameters with a mixture component variable treated as a hidden variable to facilitate improving predictions.

14. The memory storage device as recited in claim 9, the acts further comprising employing machine learning techniques that utilize known MHC-peptide binding pairs to automatically cluster different MHC proteins and learn parameters pertaining to the class of a mixed adaptive double threading model.

15. A system comprising:
one or more processors;
memory storing executable instructions that, when executed by the one or more processors, configure the one or more processors to perform acts comprising:
training data based on using a compatibility of a model;
inferring a class for a protein from the training data;
estimating one or more parameters of the binding predictor from the training data to minimize an error of approximation on the training data, each of the one or more parameters pertaining to a class of major histocompatibility complex (MHC) types;
grouping the one or more parameters pertaining to the class of MHC types to predict binding based on the training data of other MHC types;
iteratively re-inferring the class for the protein and re-estimating the one or more parameters pertaining to the class until converging to a value of about one; and
using data of the other MHC types and the grouping of the one or more parameters to predict binding for new MHC types.

16. The system as recited in claim 15, wherein iteratively re-inferring the class for the protein and re-estimating the one or more parameters pertaining to the class of the binding predictor comprises employing a stochastic gradient descent.

17. The system as recited in claim 15, wherein estimating the one or more parameters pertaining to the class of the binding predictor comprises updating a noise variance.

18. The system as recited in claim 15, the acts further comprising learning amino acid—amino acid interaction potentials and other parameters of a simplified physics-based protein binding model to facilitate optimizing fit to known binding energy and geometric configuration data.

19. The system as recited in claim 15, the acts further comprising employing a mixture model for model parameters with a mixture component variable treated as a hidden variable to facilitate improving predictions.

20. The system as recited in claim 15, the acts further comprising employing machine learning techniques that utilize known MHC-peptide binding pairs to automatically cluster different MHC proteins and learn parameters pertaining to the class of a mixed adaptive double threading model.

* * * * *